US010092303B2

(12) United States Patent
Sorensen et al.

(10) Patent No.: US 10,092,303 B2
(45) Date of Patent: Oct. 9, 2018

(54) SYSTEM FOR USE IN TISSUE REPAIR (75) Inventors: Peter Klindt Sorensen, Salem, MA (US); James Joseph Sullivan, Shrewsbury, MA (US); Paul Alexander Torrie, Marblehead, MA (US); Matthew Edwin Koski, Westford, MA (US); Roy Alan Majors, Charlotte, NC (US); Daniel B. Ellis, Holliston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/253,884

(22) Filed: Oct. 5, 2011
(Under 37 CFR 1.47)

(65) Prior Publication Data
US 2013/0035692 A1   Feb. 7, 2013

Related U.S. Application Data (60) Provisional application No. 61/390,239, filed on Oct. 6, 2010.

(51) Int. Cl.
*A61B 17/16* (2006.01)
*A61B 17/17* (2006.01)
(Continued)

(52) U.S. Cl.
CPC ...... *A61B 17/1631* (2013.01); *A61B 17/0401* (2013.01); *A61B 17/1633* (2013.01);
(Continued)

(58) Field of Classification Search
CPC . A61B 17/17; A61B 17/1735; A61B 17/1739; A61B 17/1742; A61B 17/1746; A61B 17/175; A61B 17/1753; A61B 17/1757; A61B 17/1796; A61B 17/16; A61B 17/1615; A61B 17/1631; A61B 17/1635; A61B 17/1637; A61B 17/1642; A61B 17/1664; A61B 17/8875;
(Continued)

(56) References Cited

U.S. PATENT DOCUMENTS 3,302,673 A * 2/1967 Forsberg ............. B25B 23/16
16/430
5,411,515 A * 5/1995 Haber et al. ............. 606/184
(Continued)

FOREIGN PATENT DOCUMENTS

| WO | 2009/023034 | 2/2009 |
|----|-------------|--------|
| WO | 2009023034  | 2/2009 |
| WO | WO 99/11184 | 2/2009 |

OTHER PUBLICATIONS

International Search Report and Written Opinion for PCT/US2011/054991 dated Dec. 21, 2011.
(Continued)

*Primary Examiner* — Kevin T Truong
*Assistant Examiner* — Tracy Kamikawa
(74) *Attorney, Agent, or Firm* — Norman F. Hainer, Jr.

(57) ABSTRACT

The present disclosure relates to a system for use in tissue repair. The system includes a cannulated guide, an obturator configured for insertion through the guide, a drill configured for insertion through the guide, and an anchor delivery tool configured for insertion through the guide.

17 Claims, 8 Drawing Sheets (51) Int. Cl.
*A61B 17/04* (2006.01)
*A61B 17/34* (2006.01)
*A61B 17/29* (2006.01)
*A61B 90/00* (2016.01)

(52) U.S. Cl.
CPC ....... *A61B 17/1796* (2013.01); *A61B 17/3421* (2013.01); *A61B 17/3472* (2013.01); *A61B 2017/0409* (2013.01); *A61B 2017/2904* (2013.01); *A61B 2017/3454* (2013.01); *A61B 2090/034* (2016.02); *A61B 2090/3937* (2016.02)

(58) Field of Classification Search
CPC .. A61F 2/46; A61F 2/08; A61F 2/0805; A61F 2/0811; A61F 2002/0817; A61F 2002/0841; A61F 2002/0876; A61F 2002/0882; A61F 2002/0888
USPC ............. 606/79, 80, 86 R, 96, 99, 104, 105, 606/914–916
See application file for complete search history.

(56) References Cited

U.S. PATENT DOCUMENTS

| | | | |
|---|---|---|---|
| 5,797,918 A * | 8/1998 | McGuire et al. | 606/104 |
| 5,944,739 A | 8/1999 | Zlock et al. | |
| 6,267,679 B1 * | 7/2001 | Romano | A61B 17/1642 464/58 |
| 2008/0058816 A1 * | 3/2008 | Philippon et al. | 606/72 |
| 2008/0140078 A1 * | 6/2008 | Nelson et al. | 606/80 |
| 2008/0188854 A1 | 8/2008 | Moser | |
| 2008/0294166 A1 * | 11/2008 | Goldin et al. | 606/79 |
| 2009/0062607 A1 * | 3/2009 | Kucklick et al. | 600/114 |
| 2009/0192545 A1 | 7/2009 | Workman | |
| 2010/0152739 A1 * | 6/2010 | Sidebotham et al. | 606/80 |
| 2011/0015674 A1 * | 1/2011 | Howard et al. | 606/232 |
| 2011/0218538 A1 * | 9/2011 | Sherman | A61B 17/1631 606/80 |

OTHER PUBLICATIONS

International Preliminary Report on Patentability for corresponding PCT Application No. PCT/US2011/054991, dated Apr. 18, 2013.
Office action received in corresponding Australian application No. 2011312049 dated Nov. 7, 2013.
Office action received in corresponding Japanese application No. 2013-532930 dated Sep. 16, 2015.
Office action received in corresponding Chinese application No. 201180058790.3 dated Dec. 24, 2015.
Office action received in corresponding Russian application No. 2013119871/14 dated Sep. 18, 2015.
Office action received in corresponding Mexican patent application No. MX/a/2013/003889 dated Apr. 22, 2015.
Office action received in corresponding Chinese patent application No. 201180058790.3 dated Mar. 27, 2015.
Office action received in corresponding European application No. 11770641.6-1654 dated Feb. 18, 2016.
Chinese Re-Examination Notice from corresponding International Application No. 201180058790.3, dated Jan. 15, 2018.
Office Action for CN App No. 201180058790.3 dated Apr. 28, 2018, 8 pages.

* cited by examiner

SYSTEM FOR USE IN TISSUE REPAIR

CROSS-REFERENCE TO RELATED APPLICATIONS

This application claims priority to U.S. Patent Application Ser. No. 61/390,239, the disclosure of which is incorporated herein by reference in its entirety.

BACKGROUND

Field of Technology

The present disclosure relates to tissue repair and, more specifically, to a system for use in tissue repair.

Related Art

Medical devices and methods for attaching soft tissue to bone have been developed. Of particular interest, especially in sports medicine procedures, are suture anchors. A suture anchor is typically inserted into and fixed in a bore hole drilled into a bone at a surgical repair site. Sutures are typically coupled to the anchor and are used to secure the soft tissue to the bone in order to effect the repair. For many repair procedures, accuracy in the placement of suture anchors in bone is required to achieve consistently positive surgical outcomes, requiring substantial skill on the part of the surgeon.

Accurate placement of bore holes and suture anchors can be particularly challenging when repair is performed arthroscopically, as both access to and visibility of an arthroscopic surgical site may be more limited than is the case with open surgical procedures. For example, accurately drilling bore holes and placing suture anchors into these holes, at certain joint areas of the body, can be difficult for even a very experienced surgeon. This is due to the delivery devices not being able to reach a preferred anchor delivery point, not being able to achieve the preferred anchor trajectory, or both. In addition to these access and visualization problems, current devices used in the delivery of suture anchors cannot withstand the forces imposed by new techniques.

With the increasing popularity of arthroscopic repairs on the shoulder and hip, as well as repairs in other body joints including the ankle, knee, elbow, and foot, surgeons increasingly need to perform these procedures accurately and repeatably.

Accordingly, a need exists for devices and methods that provide for the accurate placement of suture anchors used in arthroscopic surgical procedures.

SUMMARY

The present disclosure relates to a system for use in tissue repair. The system includes a cannulated guide, an obturator configured for insertion through the guide, a drill configured for insertion through the guide, and an anchor delivery tool configured for insertion through the guide.

In an embodiment, the guide includes a handle and a shaft coupled to the handle. In another embodiment, the shaft includes a distal portion angled relative to a longitudinal axis of the shaft. In yet another embodiment, the distal portion includes at least one hole. In a further embodiment, the distal portion includes a plurality of holes. In yet a further embodiment, the distal portion includes an end having a serrated edge. In an embodiment, the obturator includes a handle and a shaft coupled to the handle. In another embodiment, the shaft includes a proximal portion, a distal portion, and a portion of reduced diameter located between the proximal portion and the distal portion. In yet another embodiment, the distal portion includes a blunt end. In a further embodiment, the distal portion includes a sharp end. In yet a further embodiment, the portion of reduced diameter is flexible relative to the proximal portion.

In an embodiment, the drill includes a proximal portion, a distal portion, and a flexible portion. In another embodiment, the proximal portion includes an end configured for coupling to a drill. In yet another embodiment, the proximal portion includes a depth stop. In a further embodiment, the proximal portion includes an area of reduced diameter. In yet a further embodiment, the area includes a laser mark. In an embodiment, the distal portion includes helical threads. In another embodiment, the distal portion includes a pointed end. In yet another embodiment, the distal portion includes a laser mark. In a further embodiment, the anchor delivery tool includes a handle and a shaft coupled to the handle. In yet a further embodiment, a distal portion of the shaft includes an area of reduced diameter and a tip extending from the distal portion. In an embodiment, the distal portion is flexible relative to the proximal portion.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary nature and is in no way intended to limit the disclosure, its application, or uses.

Figure 1:
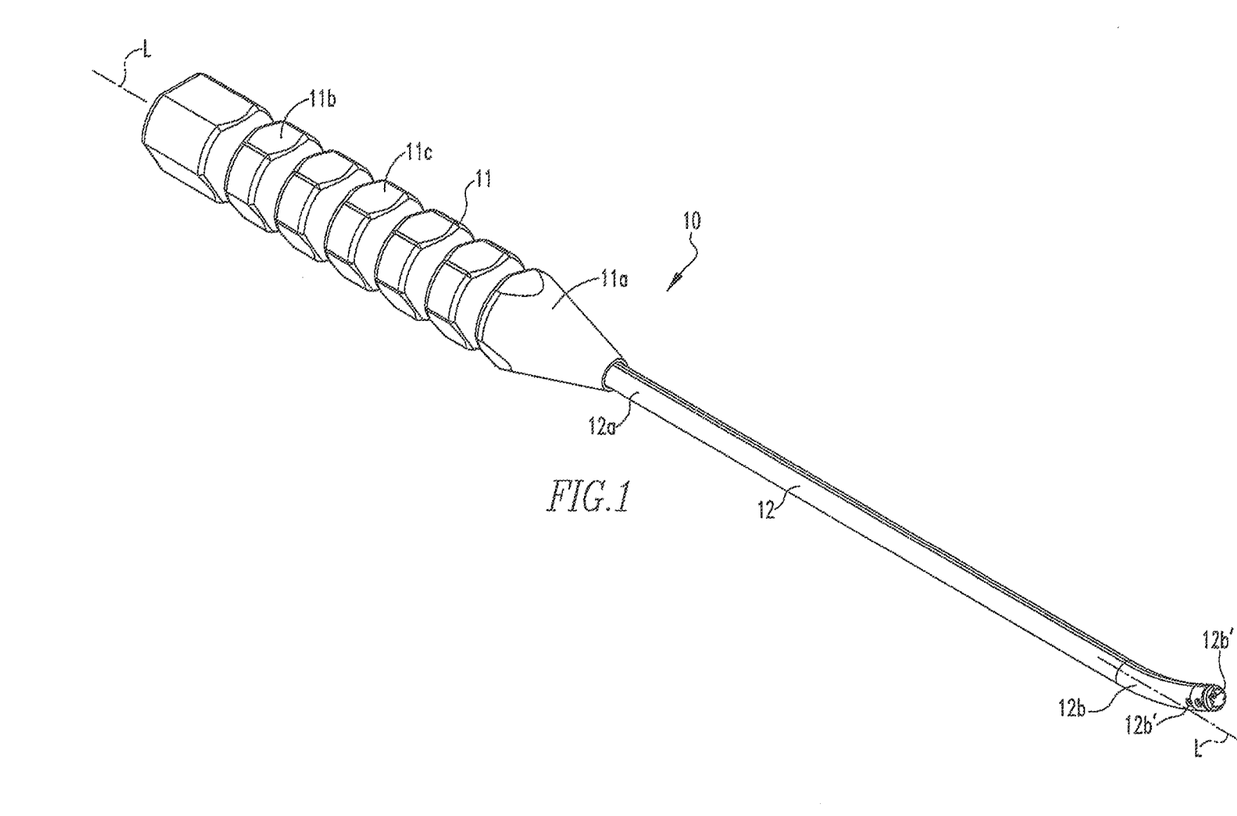
FIG. 1 shows an isometric view of the guide of the present disclosure.
Figures 2, 3:
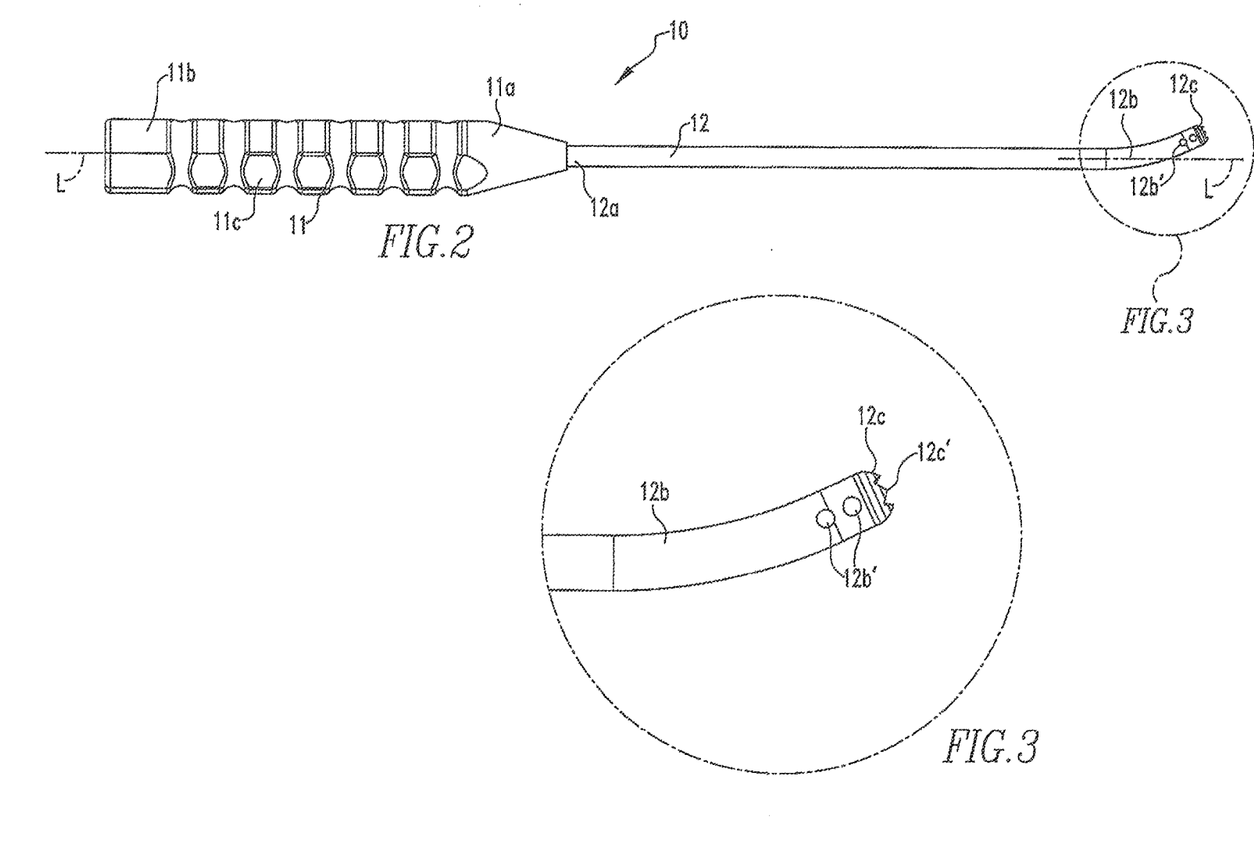
FIG. 2 shows a side view of the guide of FIG. 1.
FIG. 3 shows an exploded view of the distal portion of the guide of FIG. 1.

FIGS. 1-3 show a guide 10. The guide 10 includes a cannulated handle 11 having a distal portion 11a, a proximal portion 11b, and an outer surface 11c. The guide 10 also includes a shaft 12 coupled to the handle 11. The shaft 12 includes a proximal portion 12a and distal portion 12b. The proximal portion 12a of the shaft 12 is coupled to the distal end 11a of the handle 11. The distal portion 12b of the shaft 12 is angled relative to a longitudinal axis L of the guide 10, which allows the surgeon to achieve the ideal insertion angle of the drill at a quicker rate, thereby reducing the potential of damage to cartilage and other tissue within the joint area, as will be further described below. The distal portion 12b also includes at least one hole 12b'. For the purposes of this disclosure, the distal portion 12b includes a plurality of holes. The holes 12b' are used during surgery to view the tissue anchor and, specifically the orientation of the tissue anchor, prior to inserting the anchor into bone, as will be further described below. The holes 12b' may also be used to vent bone and other debris that may become located within the distal portion 12b of the guide 12 during surgery, as will be further described below. An end 12e of the shaft 12 includes a serrated edge 12e' for facilitating maintenance of the guide 10 on the bone during surgery, thereby substantially reducing slippage of the guide 10 off of the bone, as will be further described below. Rather than a serrated edge 12c', the end 12c may have other features known to one of skill that would help in maintaining the guide 10 on the bone and reduce slippage.

For the purposes of this disclosure, the handle 11 is manufactured from polymer material and via a molding or machining process. The shaft 12 is manufactured from metal material, such as stainless steel, and the holes 12b' and serrated edge 12e' are machined onto the shaft 12. The distal portion 12b of the guide 10 is bent or provided with an angle relative to the guide axis L via the use of a mandrel or other instrument that could be used to bend the shaft 12. Other material and processes for making the handle 11 and shaft 12 are also within the scope of this disclosure. The handle 11 and shaft 12 are coupled together via a press-fit procedure. However, other manners of coupling are also within the scope of this disclosure.

Figure 4:
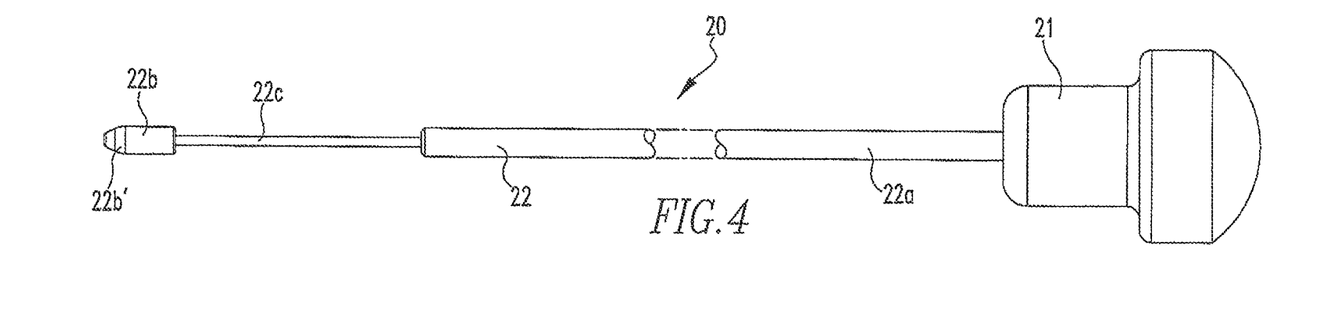
FIG. 4 shows a side view of a first embodiment of the obturator of the present disclosure.
Figure 5:
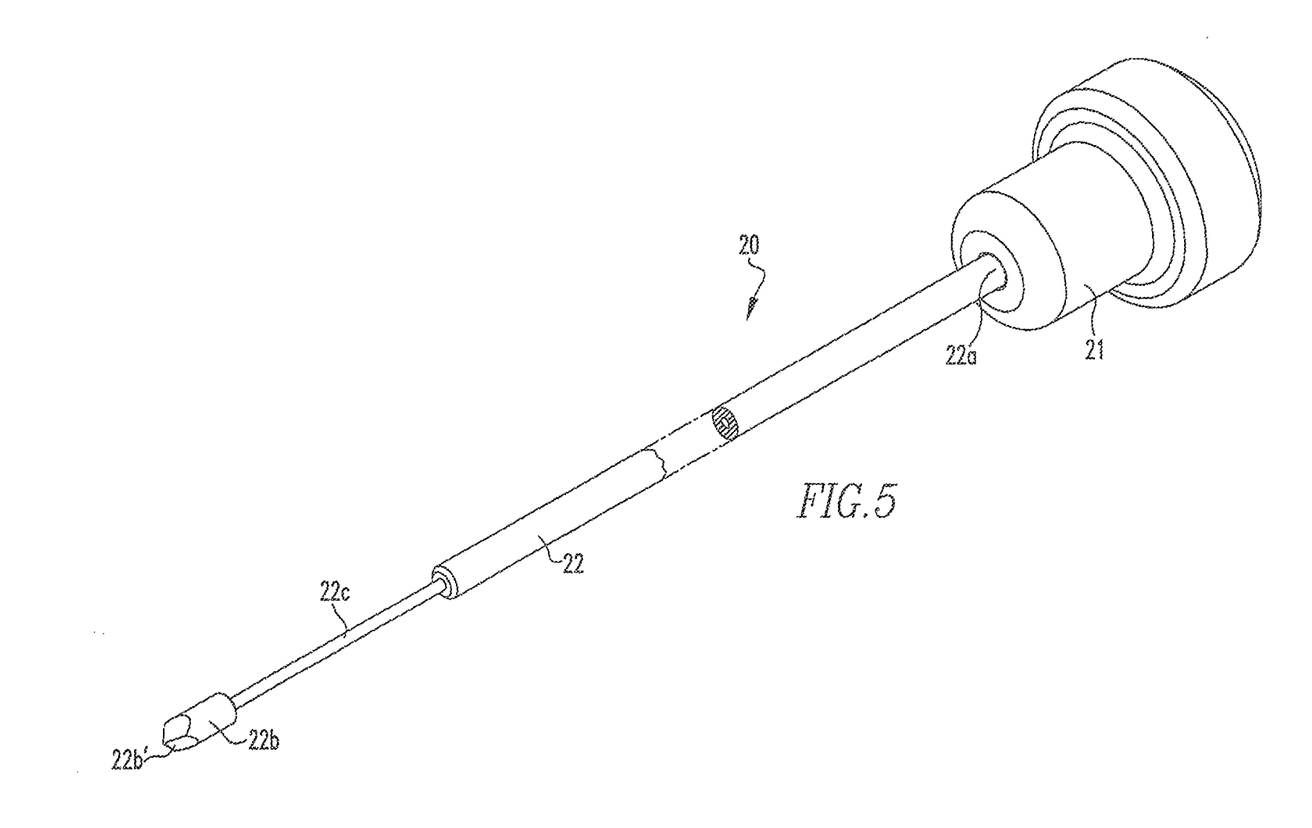
FIG. 5 shows an isometric view of a second embodiment of the obturator of the present disclosure.
Figure 6:
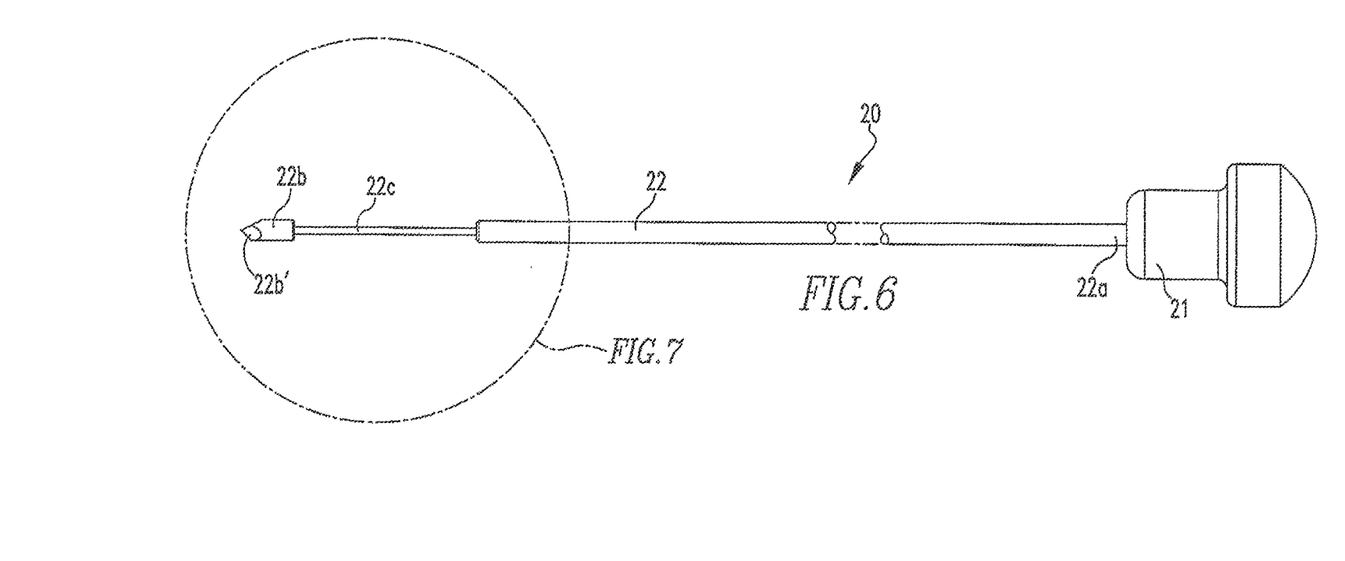
FIG. 6 shows a side view of the obturator of FIG. 5.
Figure 7:
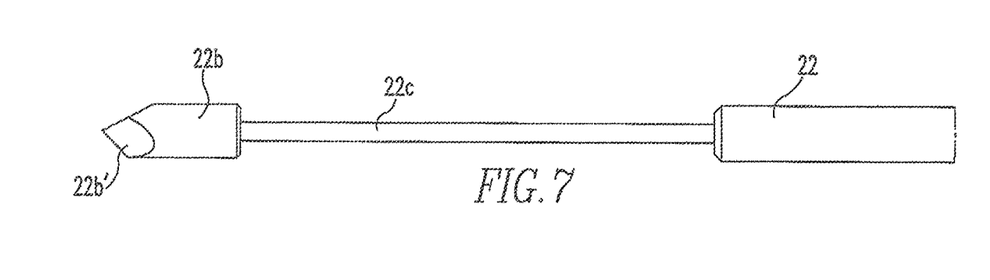
FIG. 7 shows an exploded view of the distal portion of the obturator of FIG. 5.

FIGS. 4-7 show embodiments of an obturator 20 for use with guide 10. The obturator 20 includes a handle 21 and a shaft 22 coupled to the handle 21. The shaft 22 includes a proximal portion 22a coupled to the handle 21, a distal portion 22b, and a portion 22c located between the proximal and distal portions 22a,22b having a reduced diameter relative to the diameter of the proximal and distal portions 22a,22b. The reduced diameter of portion 22c allows the portion 22c to bend when the shaft 22 is inserted through the guide 10 and the portion 22c is located within the angled distal portion 12b. FIG. 4 shows a first embodiment of the obturator 20 including a distal portion 22b having a tapered, blunt end 22b' and FIGS. 5-7 show a second obturator 20 including a distal portion 22b having a sharp end 22b'. When the shaft 22 of the obturator 20 is located within the guide 10, the end 22b' extends through end 12c, thereby reducing the possibility of the shaft end 12c, and especially the serrated edge 12c', from catching onto tissue as the guide 10 is inserted into the body, in the case of the obturator 20 having the blunt, tapered end 22b', and allowing for easier and quicker insertion of the guide 10 into the body, in the case of the obturator having the sharp end 22b', as will be further described below.

For the purposes of this disclosure, the handle 21 is made from polymer material and via a molding or machining process. The shaft 22 is made from metal and via a welding procedure. The proximal portion 22a, distal portion 22b, and portion 22c are welded together to make the shaft 22. However, a one-piece shaft is within the scope of this disclosure. The surface features of the distal portion 22b, blunt, taper or sharp, pointed features, are made via a machining process. Other material and processes for making the handle 21 and shaft 22 are also within the scope of this disclosure.

Figure 8:
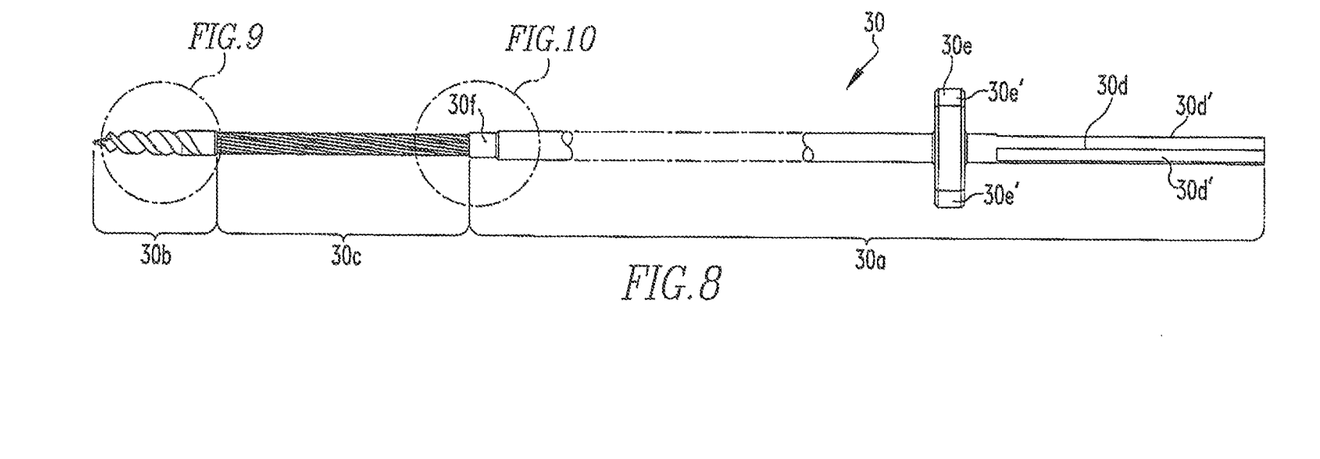
FIG. 8 shows a side view of the drill of the present disclosure.
Figure 9:
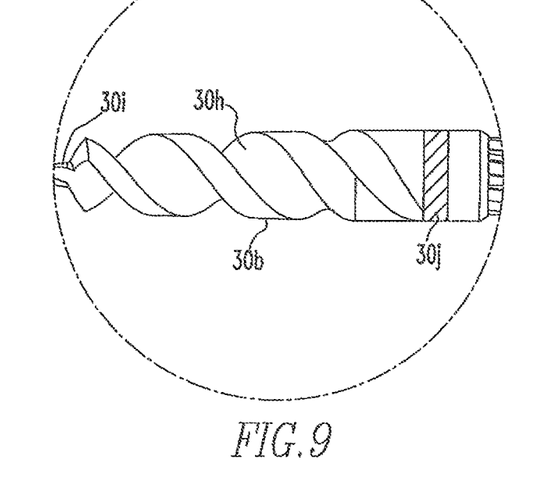
FIG. 9 shows an exploded view of the distal portion of the drill of FIG. 8.
Figure 10:
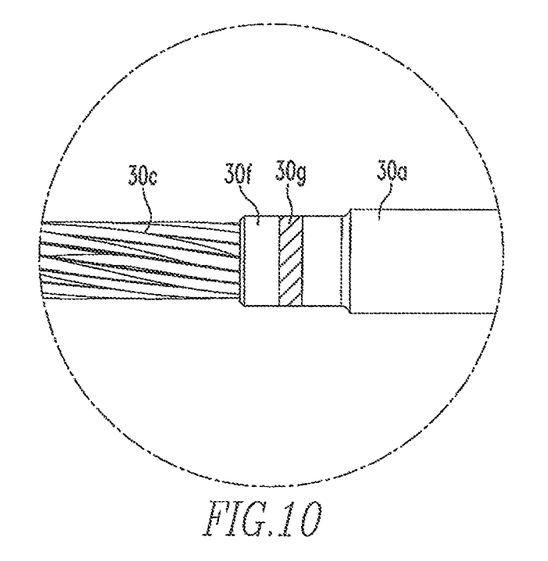
FIG. 10 shows an exploded view of the area of reduced diameter of the drill of FIG. 8.

FIGS. 8-10 show a drill 30 for use with the guide 10. The drill 30 includes a proximal portion 30a, a distal portion 30b, and a flexible portion 30c located between the proximal and distal portions 30a,30b. The proximal portion 30a includes an end 30d having flat portions 30d' configured for coupling to a drill 30, a depth stop 30e having flat sides 30e' for maintaining a location of the drill 30 while the drill 30 is sitting on a surgeon tray or table prior to use by the surgeon, and an area of reduced diameter 30f. The area 30f includes a laser weld mark 30g, the purpose of which will be described below. The flexible portion 30c extends between the area 30f and the distal portion 30b. When the drill 30 is located within the guide 10, portion 30c is located within the angled distal portion 12b and is sufficiently flexible to bend along the angle of portion 12b. The flexible portion 30c includes an inner layer of spirally wound metal wires and an outer layer of spirally would metal wires surrounding the inner layer. The inner layer also includes a through hole extending the length of the flexible portion 30c. The distal portion 30b includes helical threads 30h, a pointed end 30i, and a laser weld mark 30j. When the drill 30 is located within the guide 10, the end 30b extends through end 12c, thereby allowing the user to drill a hole in bone during surgery, as will be further described below.

For the purposes of this disclosure, the drill 30 is made from metal, such as stainless steel. The flat portions 30d',30e' of the end 30d and the depth stop 30e may be machined onto the end 30d and stop 30e. The area of reduced diameter 30f includes an inner wall having a diameter that is the same or similar to the diameter of the inner wall of the portion of the distal portion 30b that is coupled to the flexible portion 30c. The area of reduced diameter 30f is made via a machining process.

The flexible portion 30c is made via the use of a mandrel, which is removed from the through hole of the inner layer once the flexible portion 30c is made. As mentioned above, the ends of the flexible portion 30c are laser welded to the area 30f and distal portion 30b. The ends are inserted into the area 30f and distal portion 30b and then a laser is used to melt the metal material to the ends where the laser welds 30g,30j are located in FIGS. 9 and 10, thereby welding the area 30f and the distal portion 30b to the flexible portion 30c. Coupling of the flexible portion 30c to the area 30f and distal portion 30b in this manner reduces breakage or failure of the laser welds 30g,30j due to the laser welds 30g,30j being located in an area where there is the least amount of movement of the flexible portion 30c during use of the drill 30.

During use of the drill 30, the depth stop 30e abuts the handle 11, thereby substantially reducing over-insertion of the distal portion 30b into the bone, as will be further described below. The threads 30h and pointed end 30i on the distal portion 30b are made via a machining process. The drill 30 and its components and features may be made from other materials and processes known to one of skill in the art.

FIGS. 11-14 show an anchor delivery tool 40. The tool 40 includes a shaft 41 and a handle 42 coupled to the shaft 41. The shaft 41 includes a proximal portion 41a and a distal portion 41b. The distal portion 41b, as more clearly shown in FIG. 12, includes an area of reduced diameter 43 and a tip 44 that extends from the distal portion 41b. The area of reduced diameter 43 allows the shaft 41 to bend along the angled distal portion 12b when the shaft 41 is inserted through the guide 10. Prior to use, a suture anchor (not shown) is coupled to the tip 44. The suture anchor (not shown) extends through end 12c when the shaft 41 is disposed within the guide 10. The shaft 41 also includes grooves 41' for housing of suture extending from the anchor, as will be further described below.

Figures 11, 12:
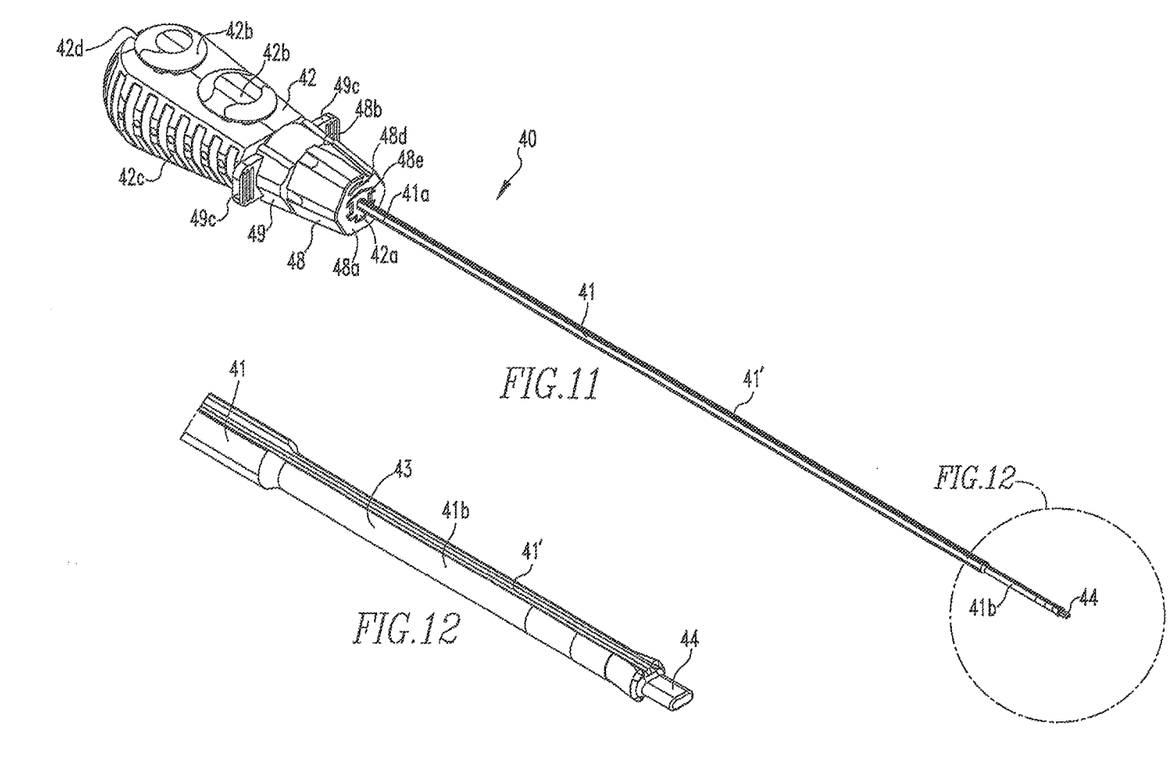
FIG. 11 shows an isometric view of the anchor delivery tool of the present disclosure.
FIG. 12 shows an exploded view of the distal portion of the anchor delivery tool of FIG. 11.
Figure 13:
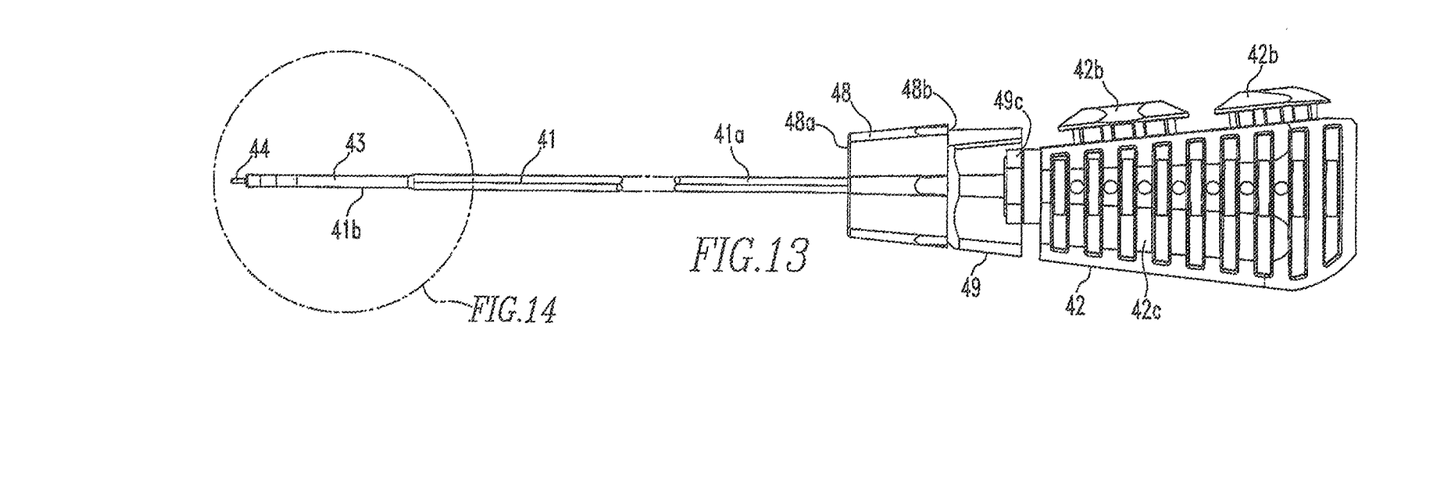
FIG. 13 shows a side view of the anchor delivery tool of the present disclosure.
Figure 14:
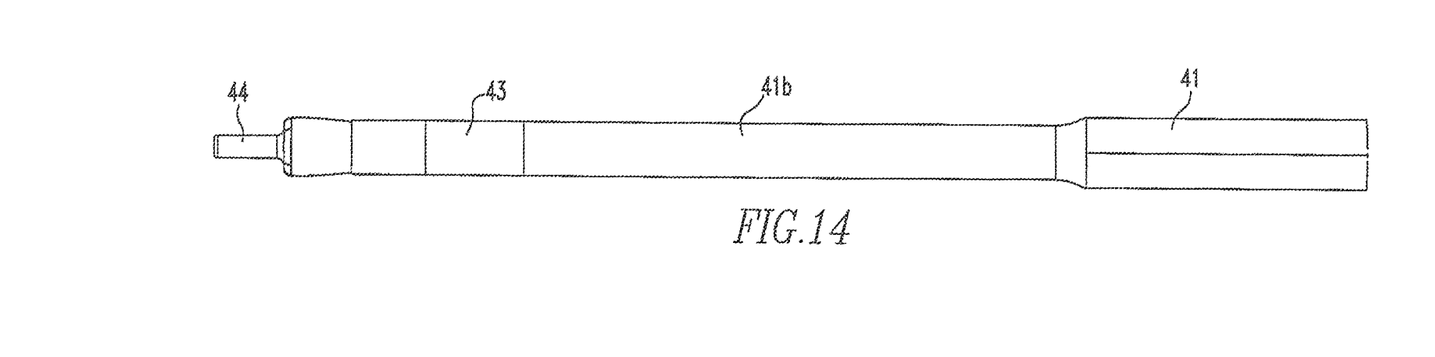
FIG. 14 shows an exploded view of the distal portion of the anchor delivery tool of FIG. 13.

The proximal portion 41a of the shaft 41 is coupled to the handle 42. The handle 42 includes a hub 42a, a nose cone 48 coupled to the hub 42a, and a knob 49 coupled to the hub 42a and located between the nose cone 48 and the handle 42. The handle 42 further includes two suture retaining features 42h, or tabs, for retaining suture during surgery, as will be further described below, laterally extending ribs 42c for maintaining a grip on the handle 42 while imparting axial compression during surgery, and a through passage 42d. The nose cone 48 includes a flat distal portion 48a, and a proximal portion 48b. In addition, the nose cone 48 includes a slotted opening 48d for housing suture during surgery, as will be further described below, and a bore 48e. The knob 49 also includes laterally extending wings 49e.

The handle 42 and shaft 41, their components, and their method of use are more fully described in International Patent Application Publication WO 2009/023034 ('034 publication), which is incorporated herein by reference in its entirety. However, the area of reduced diameter 43 is made via a machining process or other process known to one of skill in the art. In addition, the suture anchor used with the device 40 and the manner in which it is used is the same suture anchor and method of use shown in the '034 publication.

The method of tissue repair via use of the system and its components is similar to the method of tissue repair shown and described in the '034 publication. The method includes inserting the obturator through the guide, inserting the guide/obturator combination into the joint area such that the end of the guide shaft is engaged with bone, removing the obturator, inserting the drill through the guide and operating the drill to create a hole in the bone, removing the drill, inserting the shaft of the delivery device through the guide and inserting the anchor into the hole and removing the guide and delivery device. Subsequent to removal of the guide and delivery device, the soft tissue is located adjacent to the suture anchor and the suture may be pulled through the tissue and subsequently tied to fixate the tissue to the bone.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A system for use in tissue repair comprising:
a cannulated guide;
an obturator configured for insertion through the guide;
a drill configured for insertion through the guide, the drill including a proximal portion, a distal portion, and a flexible portion located between the proximal and distal portions, the drill proximal portion including a depth stop, flat portions, and an area of reduced diameter, the depth stop including flat sides and the area of reduced diameter including a cavity and a laser weld mark spaced away from a distal edge of the area of reduced diameter, the drill distal portion including a sleeve portion and helical threads with a pointed end, and a laser weld mark disposed on a proximal edge of the helical threads and spaced away from a proximal edge of the sleeve portion, ends of the flexible portion extending within and attached to the cavity and the sleeve portion via the laser welds; and
an anchor delivery tool configured for insertion through the guide, the anchor delivery tool including a handle and a shaft coupled to the handle, the shaft including a proximal portion, a distal portion having a smaller diameter than the proximal portion, and a tip extending from the distal portion, the entire tip having a smaller diameter than the distal portion,
wherein the flexible portion has a diameter that is smaller than a diameter of the area of reduced diameter and a diameter of the distal portion of the drill.

2. The system of claim 1 wherein the guide includes a guide handle and a guide shaft coupled to the guide handle.

3. The system of claim 2 wherein the guide shaft includes a distal portion angled relative to a longitudinal axis of the guide shaft.

4. The system of claim 3 wherein the distal portion of the guide shaft includes at least one hole.

5. The system of claim 3 wherein the distal portion of the guide shaft includes a plurality of holes axially spaced along a first side of a guide distal end.

6. The system of claim 3 wherein the distal portion of the guide shaft includes an end having a serrated edge.

7. The system of claim 1 wherein the obturator includes an obturator handle and an obturator shaft coupled to the obturator handle.

8. The system of claim 7 wherein the obturator shaft is a single piece shaft, including a proximal portion having a first length, a portion of reduced diameter extending from the proximal portion having a second length and a distal portion having a diameter different than and extending from the portion of reduced diameter, the second length shorter than the first length.

9. The system of claim 8 wherein the obturator shaft distal portion includes a blunt end.

10. The system of claim 8 wherein the obturator shaft distal portion includes a sharp end.

11. The system of claim 8 wherein the obturator shaft portion of reduced diameter is flexible relative to the obturator shaft proximal portion.

12. The system of claim 8 wherein the portion of reduced diameter is spaced away from the obturator handle by the first length and is substantially closer to a shaft distal terminus than the obturator handle.

13. The system of claim 8 wherein the portion of reduced diameter and the drill flexible portion have substantially similar lengths.

14. The system of claim 1 wherein the shaft has a solid construction throughout.

15. The system of claim 1 wherein the tip is non-cannulated.

16. The system of claim 1 wherein the flexible portion includes an inner layer comprising a plurality of spirally wound metal wires, and an outer layer comprising a plurality of spirally wound metal wires surrounding the inner layer, and a through hole extending the length of the flexible portion.

17. The system of claim 16 wherein the inner and outer layers of spirally wound metal wires of the flexible portion extend within and are coupled to the area of reduced diameter and the sleeve portion of the drill via the laser welds.

\* \* \* \* \*